United States Patent
Pelled et al.

(10) Patent No.: US 10,232,564 B2
(45) Date of Patent: Mar. 19, 2019

(54) LAMINATED SEALING MEMBER FOR PROSTHETIC HEART VALVE

(71) Applicant: Edwards Lifesciences Corporation, Irvine, CA (US)

(72) Inventors: Itai Pelled, Ramat-Hasharon (IL); Elena Sherman, Pardes Hanna (IL); Eran Goldberg, Nesher (IL); Kevin D. Rupp, Irvine, CA (US); Noam Nir, Gesher Haziv (IL)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/140,387

(22) Filed: Apr. 27, 2016

(65) Prior Publication Data

US 2016/0317305 A1 Nov. 3, 2016

Related U.S. Application Data

(60) Provisional application No. 62/154,610, filed on Apr. 29, 2015.

(51) Int. Cl.
*A61F 2/24* (2006.01)
*B29C 65/00* (2006.01)

(52) U.S. Cl.
CPC ...... *B29C 66/53245* (2013.01); *A61F 2/2412* (2013.01); *A61F 2/2415* (2013.01);
(Continued)

(58) Field of Classification Search
CPC ............ A61F 2/2418; A61F 2210/0061; A61F 2250/0069; A61F 2/2409; A61F 2220/005;
(Continued)

(56) References Cited

U.S. PATENT DOCUMENTS 3,744,060 A * 7/1973 Bellhouse ............. A61F 2/2409
137/849
3,755,823 A 9/1973 Hancock
(Continued)

FOREIGN PATENT DOCUMENTS

DE 19532846 A1 3/1997
DE 19546692 A1 6/1997
(Continued)

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3. pp. 305-311. 1989.
(Continued)

*Primary Examiner* — Seema Mathew
(74) *Attorney, Agent, or Firm* — Joel B. German; AnneMarie Kaiser; Klarquist Sparkman, LLP

(57) ABSTRACT

The present disclosure relates to laminated sealing members for prosthetic valves and methods of making the same. In a representative embodiment, an implantable prosthetic valve that is radially collapsible to a collapsed configuration and radially expandable to an expanded configuration comprises an annular frame having an inflow end and an outflow end, a leaflet structure positioned within the frame and secured thereto, and a laminate sealing member comprising an encapsulating material. The laminate sealing member has a main portion that encapsulates at least a portion of the frame and an end portion extending from the inflow end of the frame, and the end portion of the laminate sealing member is folded to form a cuff adjacent the inflow end of the frame and secured to the main portion of the laminate sealing member.

20 Claims, 9 Drawing Sheets

(52) U.S. Cl.
CPC ........... *A61F 2/2418* (2013.01); *A61F 2/2433* (2013.01); *A61F 2210/0076* (2013.01); *A61F 2230/0069* (2013.01); *A61F 2240/001* (2013.01); *A61F 2250/0069* (2013.01)

(58) Field of Classification Search
CPC ...... A61F 2220/0075; A61F 2230/0054; A61F 2/24; A61F 2/2412; A61F 2002/0086; A61F 2220/0058; A61F 2250/0097; A61F 2/2415; A61F 2230/005; A61F 2230/0065; A61F 2230/0069; A61F 2230/0091; A61F 2250/0003; A61F 2250/0036; A61F 2250/0039; A61F 2250/0056; A61F 2250/006; A61F 2250/0063; A61F 2/0095; A61F 2/2427; A61F 2/2433; A61F 2/2436; A61F 2/246; A61F 2210/0076; A61F 2/08
See application file for complete search history.

(56) References Cited

U.S. PATENT DOCUMENTS

| | | | |
|---|---|---|---|
| 3,983,581 A | 10/1976 | Angell et al. |
| 4,035,849 A | 7/1977 | Angell et al. |
| 4,777,951 A | 10/1988 | Cribier et al. |
| 4,787,899 A | 11/1988 | Lazarus |
| 4,796,629 A | 1/1989 | Grayzel |
| 4,856,516 A | 8/1989 | Hillstead |
| 4,878,495 A | 11/1989 | Grayzel |
| 4,966,604 A | 10/1990 | Reiss |
| 4,994,077 A | 2/1991 | Dobben |
| 5,059,177 A | 10/1991 | Towne et al. |
| 5,192,297 A | 3/1993 | Hull |
| 5,282,847 A | 2/1994 | Trescony et al. |
| 5,370,685 A | 12/1994 | Stevens |
| 5,411,552 A | 5/1995 | Andersen et al. |
| 5,545,214 A | 8/1996 | Stevens |
| 5,554,185 A | 9/1996 | Block et al. |
| 5,558,644 A | 9/1996 | Boyd et al. |
| 5,584,803 A | 12/1996 | Stevens et al. |
| 5,591,195 A | 1/1997 | Taheri et al. |
| 5,607,464 A | 3/1997 | Trescony et al. |
| 5,628,786 A | 5/1997 | Banas et al. |
| 5,665,115 A | 9/1997 | Cragg |
| 5,769,812 A | 6/1998 | Stevens et al. |
| 5,776,188 A | 7/1998 | Shepherd et al. |
| 5,800,508 A | 9/1998 | Goicoechea et al. |
| 5,840,081 A | 11/1998 | Andersen et al. |
| 5,843,161 A | 12/1998 | Solovay |
| 5,855,597 A | 1/1999 | Jayaraman |
| 5,925,063 A | 7/1999 | Khosravi |
| 5,957,949 A | 9/1999 | Leonhardt et al. |
| 6,027,525 A | 2/2000 | Suh et al. |
| 6,110,198 A | 8/2000 | Fogarty et al. |
| 6,168,614 B1 | 1/2001 | Andersen et al. |
| 6,221,091 B1 | 4/2001 | Khosravi |
| 6,245,102 B1 | 6/2001 | Jayaraman |
| 6,302,906 B1 | 10/2001 | Goecoechea et al. |
| 6,306,164 B1 | 10/2001 | Kujawski |
| 6,352,554 B2 | 3/2002 | De Paulis |
| 6,425,916 B1 | 7/2002 | Garrison et al. |
| 6,454,799 B1 | 9/2002 | Schreck |
| 6,458,153 B1 | 10/2002 | Bailey et al. |
| 6,461,382 B1 | 10/2002 | Cao |
| 6,482,228 B1 | 11/2002 | Norred |
| 6,527,979 B2 | 3/2003 | Constantz |
| 6,582,462 B1 | 6/2003 | Andersen et al. |
| 6,652,578 B2 | 11/2003 | Bailey et al. |
| 6,729,356 B1 | 5/2004 | Baker et al. |
| 6,730,118 B2 | 5/2004 | Spenser et al. |
| 6,733,525 B2 | 5/2004 | Yang et al. |
| 6,767,362 B2 | 7/2004 | Schreck |
| 6,814,754 B2 | 11/2004 | Greenhalgh |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,911,040 B2 | 6/2005 | Johnson et al. |
| 7,018,406 B2 | 3/2006 | Seguin et al. |
| 7,018,408 B2 | 3/2006 | Bailey et al. |
| 7,147,663 B1 | 12/2006 | Berg et al. |
| 7,264,632 B2 | 9/2007 | Wright et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,585,321 B2 | 9/2009 | Cribier |
| 7,618,446 B2 | 11/2009 | Andersen et al. |
| 7,655,034 B2 | 2/2010 | Mitchell et al. |
| 7,785,366 B2 | 8/2010 | Maurer et al. |
| 7,959,672 B2 | 6/2011 | Salahieh et al. |
| 7,993,394 B2 | 8/2011 | Hariton et al. |
| 8,029,556 B2 | 10/2011 | Rowe |
| 8,167,932 B2 | 5/2012 | Bourang |
| 8,403,983 B2 | 3/2013 | Quadri et al. |
| 8,449,606 B2 | 5/2013 | Eliasen et al. |
| 8,992,608 B2 | 3/2015 | Haug et al. |
| 2001/0027338 A1 | 10/2001 | Greenberg |
| 2002/0026094 A1 | 2/2002 | Roth |
| 2002/0032481 A1 | 3/2002 | Gabbay |
| 2002/0138135 A1 | 9/2002 | Duerig et al. |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0043760 A1* | 2/2005 | Fogarty ............. A61B 17/0401 606/224 |
| 2005/0096736 A1 | 5/2005 | Osse et al. |
| 2005/0137682 A1* | 6/2005 | Justino ................. A61F 2/2412 623/1.24 |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2005/0273160 A1* | 12/2005 | Lashinski ............ A61F 2/2436 623/1.25 |
| 2006/0025857 A1 | 2/2006 | Bergheim et al. |
| 2006/0058872 A1 | 3/2006 | Salahieh et al. |
| 2006/0149350 A1 | 7/2006 | Patel et al. |
| 2007/0005131 A1 | 1/2007 | Taylor |
| 2007/0010877 A1 | 1/2007 | Salahieh et al. |
| 2007/0112422 A1 | 5/2007 | Dehdashtian |
| 2007/0142907 A1* | 6/2007 | Moaddeb ............. A61F 2/2418 623/2.11 |
| 2007/0203503 A1 | 8/2007 | Salahieh et al. |
| 2007/0203575 A1 | 8/2007 | Forster et al. |
| 2007/0265700 A1 | 11/2007 | Eliasen et al. |
| 2008/0114442 A1 | 5/2008 | Mitchell et al. |
| 2008/0125853 A1 | 5/2008 | Bailey et al. |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0319037 A1 | 12/2009 | Rowe et al. |
| 2010/0036484 A1* | 2/2010 | Hariton ................ A61F 2/2412 623/2.18 |
| 2010/0049313 A1 | 2/2010 | Alon et al. |
| 2010/0174364 A1* | 7/2010 | Hoffman .............. A61F 2/2412 623/2.17 |
| 2010/0185277 A1* | 7/2010 | Braido ................. A61F 2/2412 623/2.18 |
| 2010/0198347 A1 | 8/2010 | Zakay et al. |
| 2011/0015729 A1 | 1/2011 | Jimenez et al. |
| 2012/0123529 A1 | 5/2012 | Levi et al. |
| 2012/0253453 A1* | 10/2012 | Bruchman ............. A61L 27/48 623/1.24 |
| 2012/0296418 A1* | 11/2012 | Bonyuet .............. A61F 2/2415 623/2.18 |

(56) References Cited

U.S. PATENT DOCUMENTS

| | | | |
|---|---|---|---|
| 2013/0023985 A1 | 1/2013 | Khairkhahan et al. | |
| 2013/0038765 A1 | 2/2013 | Fujisaki | |
| 2013/0317598 A1 | 11/2013 | Rowe et al. | |
| 2013/0338765 A1 | 12/2013 | Braido et al. | |
| 2014/0128964 A1* | 5/2014 | Delaloye | A61F 2/2418 623/2.11 |
| 2014/0155997 A1* | 6/2014 | Braido | A61F 2/2418 623/2.37 |
| 2014/0194981 A1* | 7/2014 | Menk | A61F 2/2418 623/2.17 |
| 2014/0209238 A1 | 7/2014 | Bonyuet et al. | |
| 2014/0277402 A1 | 9/2014 | Essinger et al. | |
| 2016/0374802 A1 | 12/2016 | Levi et al. | |
| 2018/0360598 A1 | 12/2018 | Bonyuet et al. | |

FOREIGN PATENT DOCUMENTS

| | | |
|---|---|---|
| DE | 19857887 A1 | 7/2000 |
| DE | 19907646 A1 | 8/2000 |
| EP | 0103546 A1 | 3/1984 |
| EP | 0592410 A1 | 4/1994 |
| EP | 0597967 A1 | 5/1994 |
| EP | 0850607 A1 | 7/1998 |
| EP | 1796597 A2 | 6/2007 |
| FR | 2788217 A1 | 7/2000 |
| FR | 2815844 A1 | 5/2002 |
| SU | 1271508 A1 | 11/1986 |
| WO | 91/17720 A1 | 11/1991 |
| WO | 1993001768 A1 | 2/1993 |
| WO | 98/29057 A1 | 7/1998 |
| WO | 1999040964 A1 | 8/1999 |
| WO | 1999047075 A1 | 9/1999 |
| WO | 01/49213 A2 | 7/2001 |
| WO | 0154625 A1 | 8/2001 |
| WO | 01/76510 A2 | 10/2001 |
| WO | 02/22054 A1 | 3/2002 |
| WO | 02/36048 A1 | 5/2002 |
| WO | 02/47575 A2 | 6/2002 |
| WO | 0347468 A1 | 6/2003 |
| WO | 2005034812 A1 | 4/2005 |
| WO | 2005084595 A1 | 9/2005 |
| WO | 2005102015 A2 | 11/2005 |
| WO | 2006111391 A1 | 10/2006 |
| WO | 2006/138173 A2 | 12/2006 |
| WO | 2007047488 A2 | 4/2007 |
| WO | 2007067942 A1 | 6/2007 |
| WO | 2007097983 A2 | 8/2007 |
| WO | 2008/005405 A2 | 1/2008 |
| WO | 2008091515 A2 | 7/2008 |
| WO | 2009033469 A1 | 3/2009 |
| WO | 2010121076 A2 | 10/2010 |

OTHER PUBLICATIONS

Bailey, S. "Percutaneous Expandable Prosthetic Valves," Textbook of Interventional Cardiology vol. 2, 2nd Ed. pp. 1268-1276. 1994.

H.R. Andersen "History of Percutaneous Aortic Valve Prosthesis," Herz No. 34. pp. 343-346. 2009.

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Uchida, "Modifications of Gianturco Expandable Wire Stents," American Journal of Roentgenology, vol. 150. pp. 1185-1187. 1986.

Wheatley, "Valve Prostheses," Operative Surgery, 4th ed. pp. 415-424. 1986.

International Search Report from corresponding PCT case No. PCT/US2016/029769 dated Jul. 29, 2016.

* cited by examiner

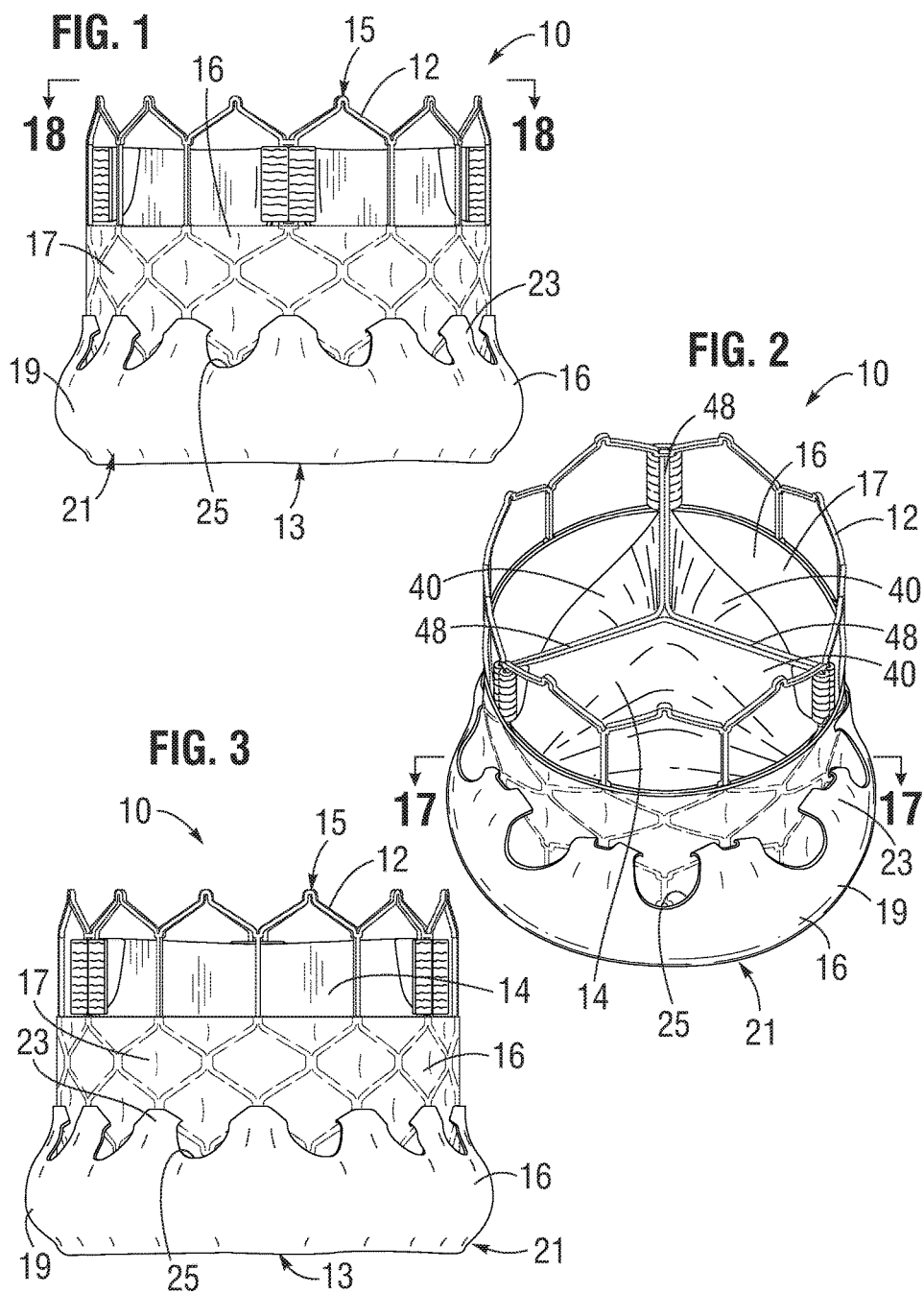

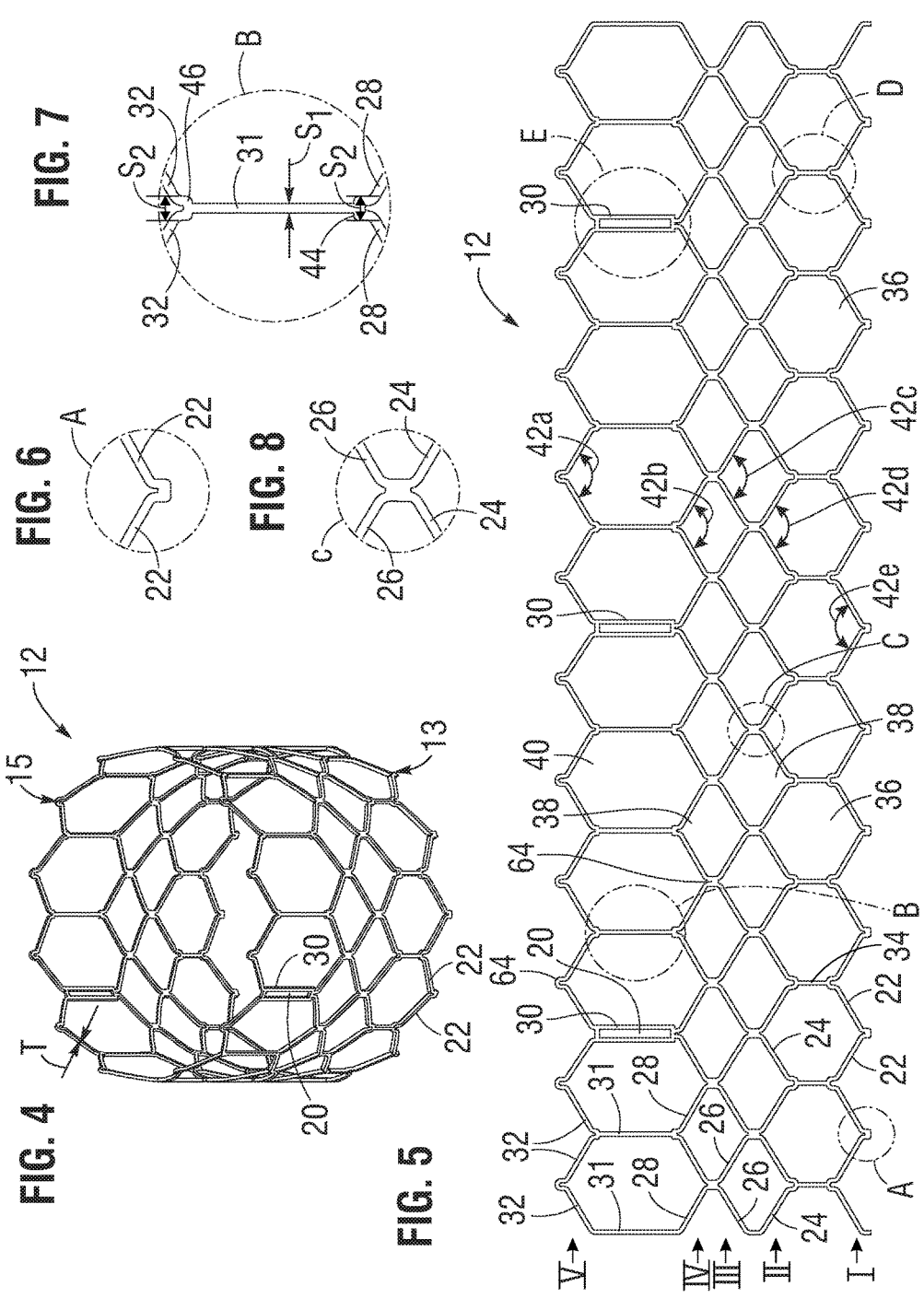

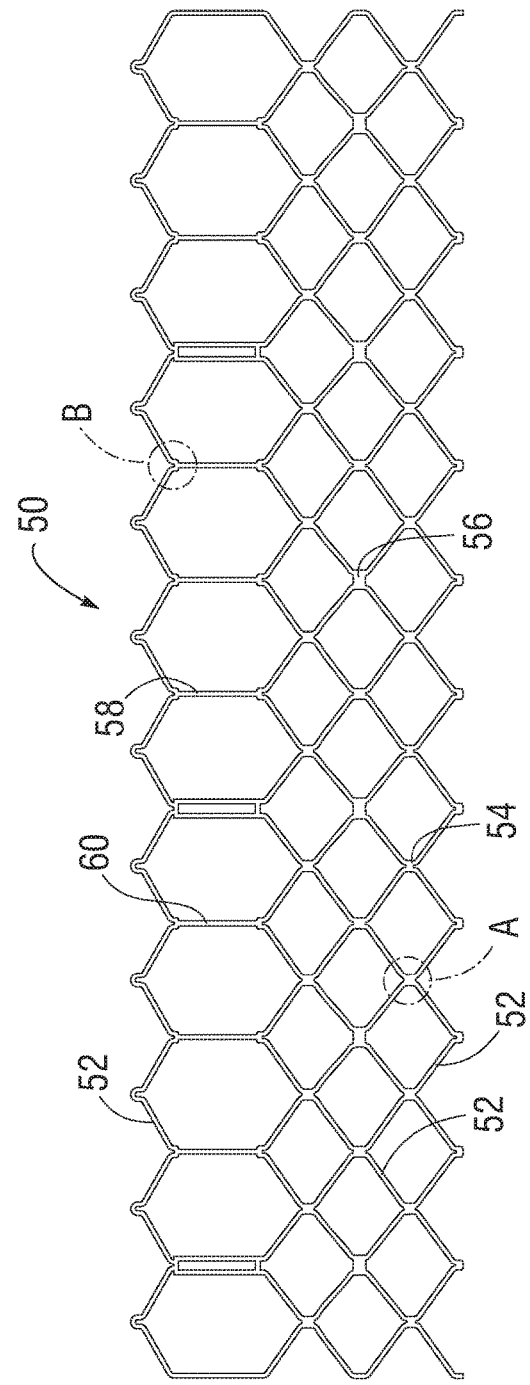
FIG. 12
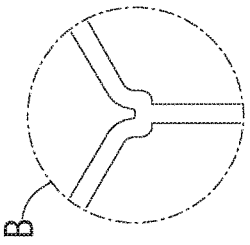
FIG. 13
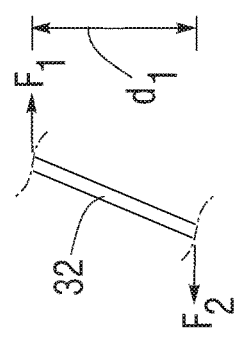
FIG. 14
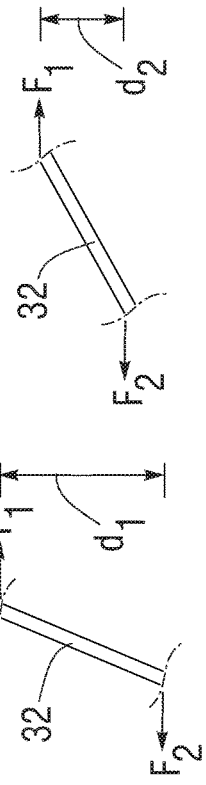
FIG. 15A
FIG. 15B

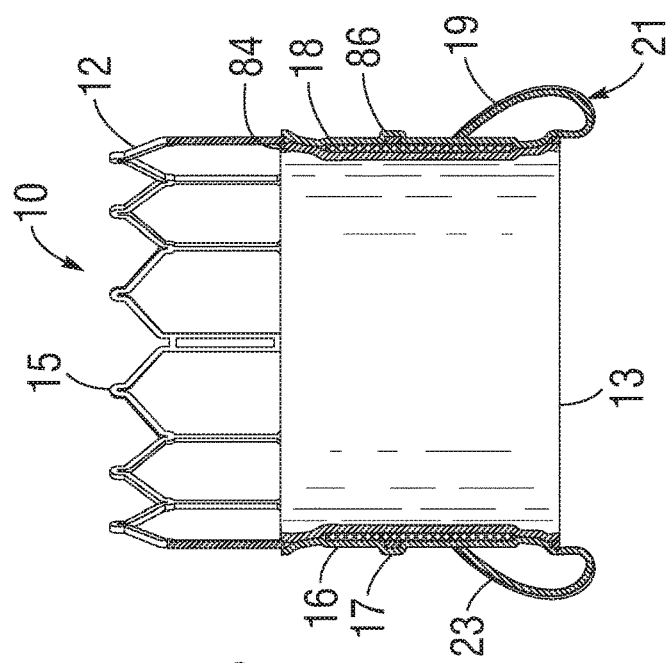
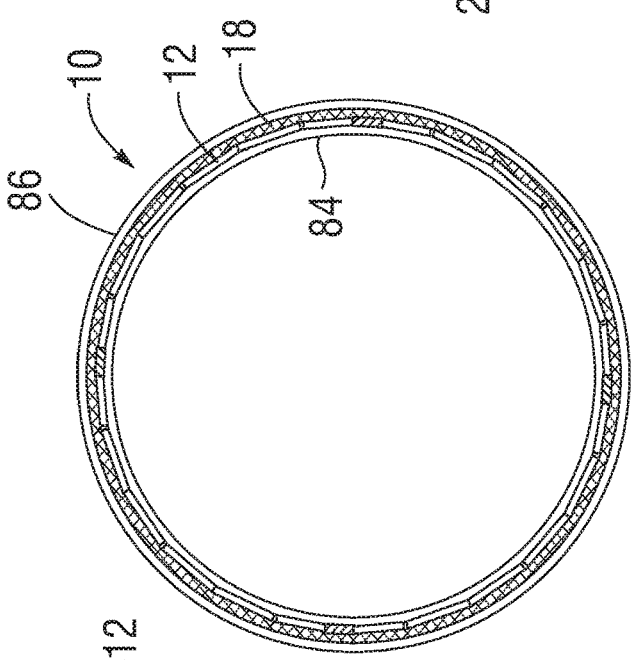
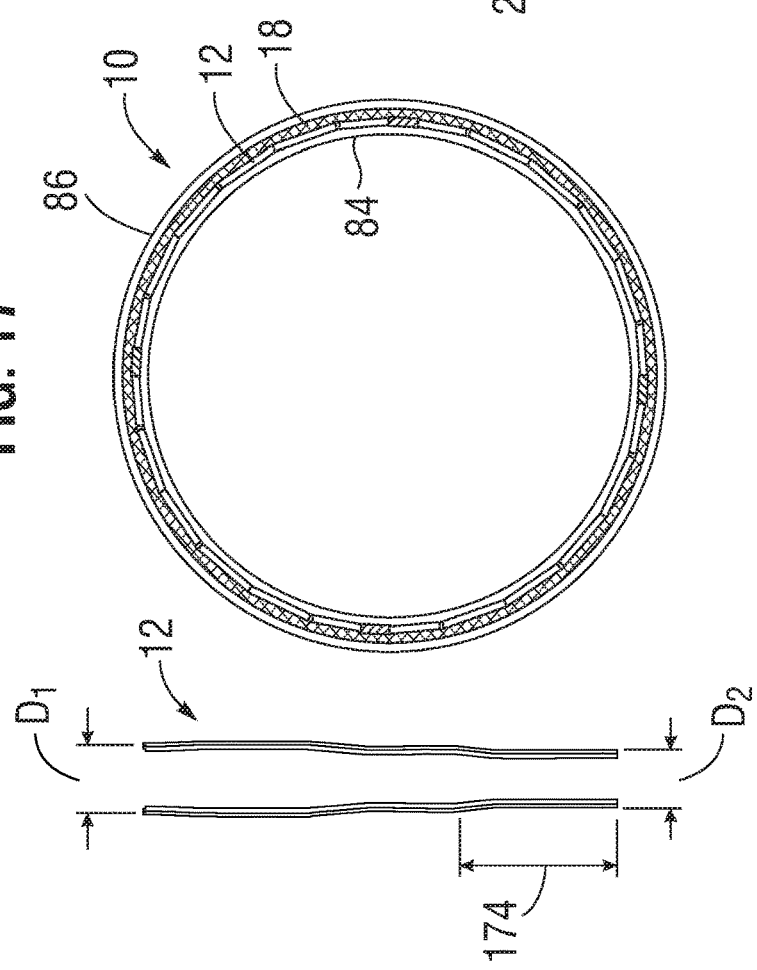

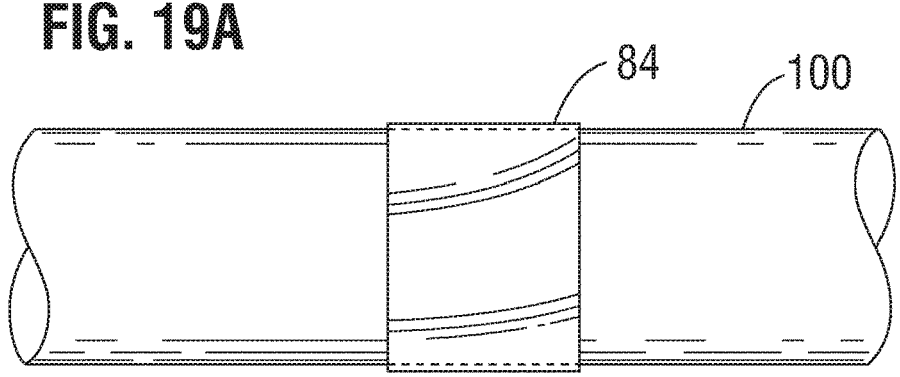
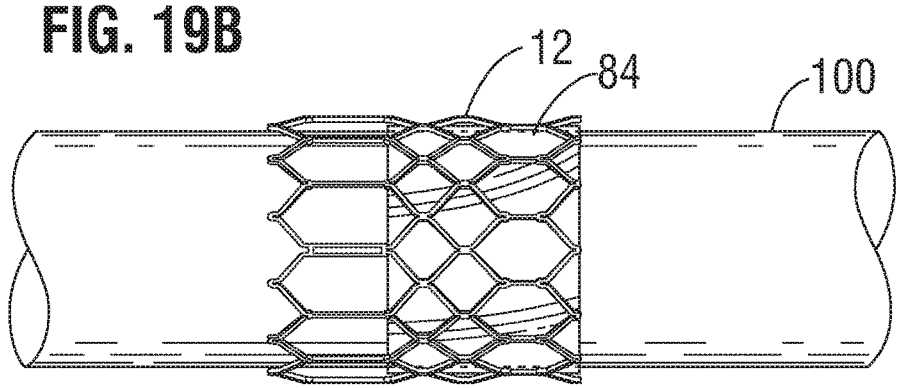
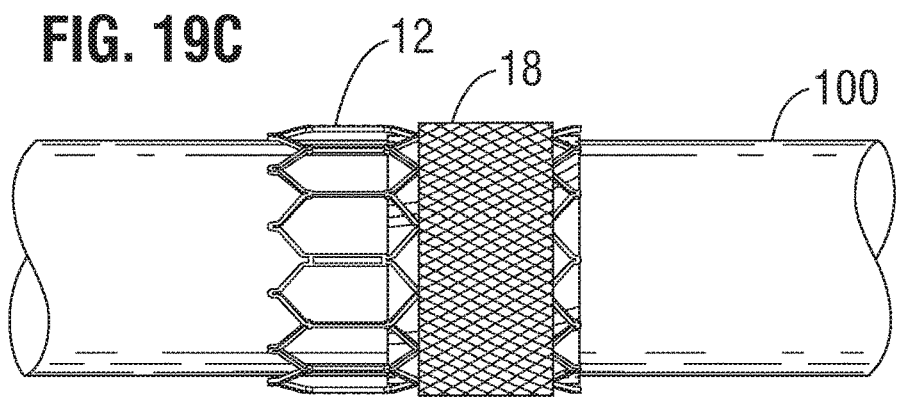

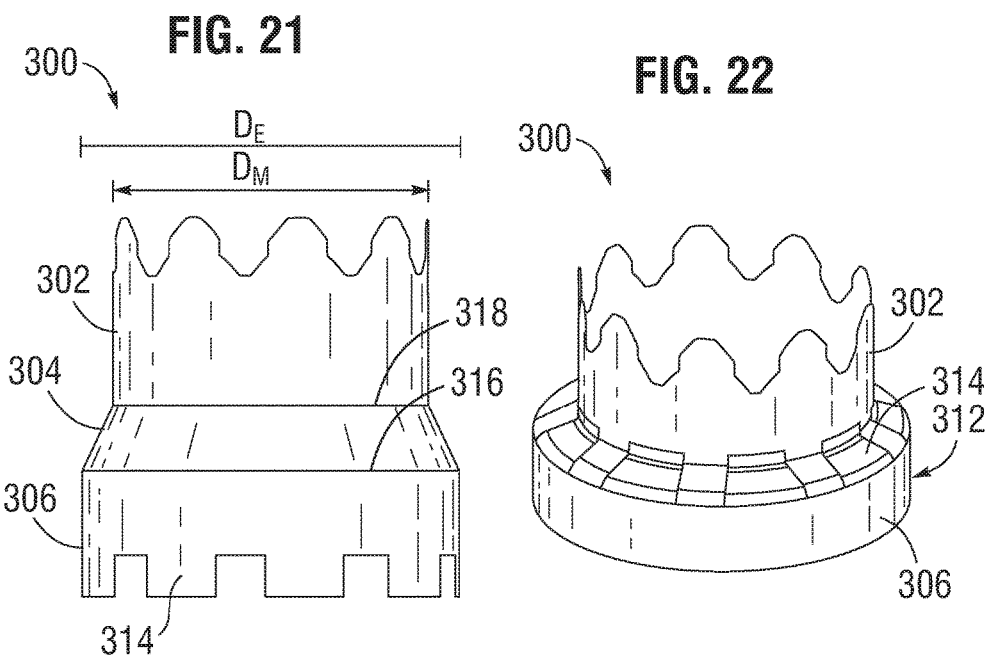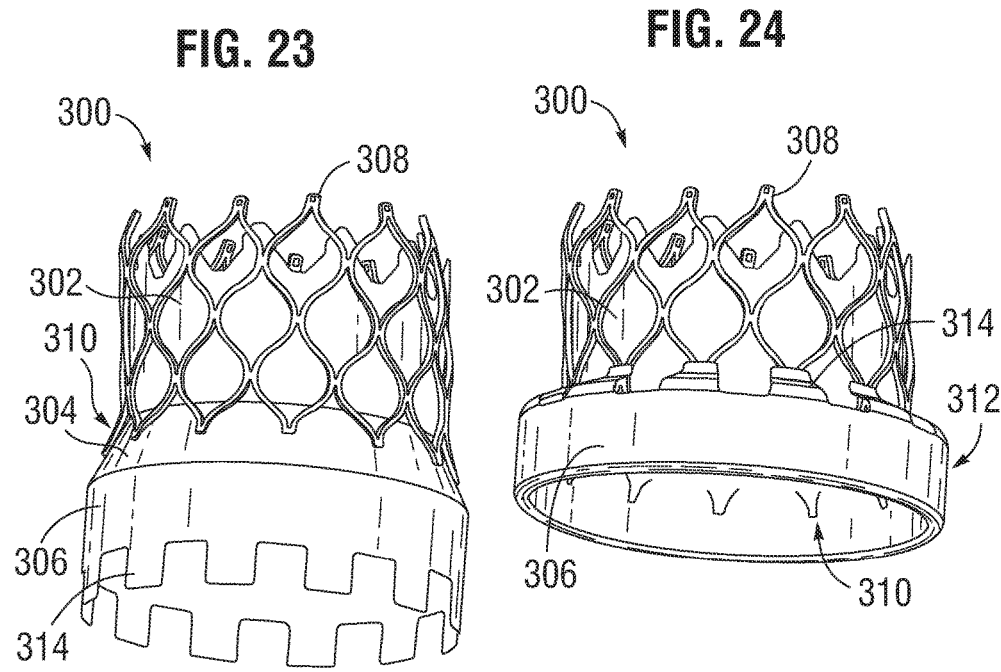

LAMINATED SEALING MEMBER FOR PROSTHETIC HEART VALVE

CROSS REFERENCE TO RELATED APPLICATION

This application claims the benefit of U.S. Provisional Patent Application No. 62/154,610, filed Apr. 29, 2015, which is incorporated herein by reference in its entirety.

FIELD

The present disclosure relates to implantable prosthetic valves and, more particularly, to laminated sealing members for prosthetic valves and methods of making the same.

BACKGROUND

Known prosthetic valves include a frame with a valvular structure mounted therein, an inner skirt or sealing member secured to the inside of the frame, and an outer skirt or sealing member secured to the exterior of the frame. The inner and outer skirts frequently must be secured to the frame by suturing or stitching the fabric of the respective skirts to the frame. Such suturing must often be done by hand, increasing the cost and time required to produce a prosthetic valve. Accordingly, improvements to skirts for prosthetic valves are desirable.

SUMMARY

Certain embodiments of the disclosure concern laminated sealing members for prosthetic heart valves and methods of making the same. In one representative embodiment, an implantable prosthetic valve that is radially collapsible to a collapsed configuration and radially expandable to an expanded configuration comprises an annular frame having an inflow end and an outflow end, a leaflet structure positioned within the frame and secured thereto, and a laminate sealing member comprising an encapsulating material. The laminate sealing member has a main portion that encapsulates at least a portion of the frame and an end portion extending from the inflow end of the frame, and the end portion of the laminate sealing member is folded to form a cuff adjacent the inflow end of the frame and secured to the main portion of the laminate sealing member.

In another representative embodiment, a method of making a prosthetic heart valve comprises positioning a first layer about a mandrel, positioning a radially expandable frame over the first layer, and positioning a second layer over the radially expandable frame. The method further comprises fusing the first and second layers to form a monolithic laminate sealing member such that at least a portion of the frame is encapsulated within the laminate sealing member, and folding an end portion of the laminate sealing member and securing it to a main portion of the laminate sealing member to form a cuff adjacent an inflow end of the frame.

In another representative embodiment, a transcatheter heart valve comprises a radially expandable frame having an inflow end, an outflow end, and a laminate sealing member comprising a non-fabric inner layer positioned inside of the frame, a non-fabric outer layer positioned outside of the frame, and a fabric layer positioned between the non-fabric inner layer and the non-fabric outer layer. The non-fabric inner and outer layers are fused to one another such that the fabric layer and at least a portion of the frame are encapsulated therebetween. The laminate sealing member further comprises a main portion adjacent the frame and an end portion extending from the inflow end of the frame, the end portion being folded to form a cuff adjacent the inflow end of the frame and secured to the main portion of the laminate sealing member.

The foregoing and other objects, features, and advantages of the disclosure will become more apparent from the following detailed description, which proceeds with reference to the accompanying figures.

BRIEF DESCRIPTION OF THE DRAWINGS

FIGS. 1-3 illustrate an exemplary embodiment of a prosthetic valve including a laminate sealing member FIGS. 4-10 illustrate an exemplary frame of the heart valve of FIG. 1.

FIGS. 11-15B illustrate another embodiment of a frame for use with a prosthetic heart valve.

FIG. 16 illustrates a cross-sectional profile of the frame of FIG. 4, showing a general tapering from the outflow end to the inflow end.

FIG. 17 is a cross-sectional view of the prosthetic heart valve of FIG. 2 taken along line 17-17.

FIG. 18 is a cross-sectional view of the prosthetic heart valve of FIG. 1 taken along line 18-18.

FIGS. 19A-19F illustrate a method of forming a laminate sealing member on the frame of a prosthetic heart valve, according to one embodiment.

FIG. 21 is a side elevation view illustrating another embodiment of a sealing member.

FIG. 22 is a perspective view of the sealing member of FIG. 21 folded to form a cuff.

FIG. 23 is a perspective view illustrating the main portion of the sealing member of FIG. 21 secured to a frame and the end portion extending distally from the frame.

FIG. 24 is a perspective view illustrating the end portion of the sealing member of FIG. 21 folded and secured to the frame to form a cuff.

DETAILED DESCRIPTION

Figure 9:
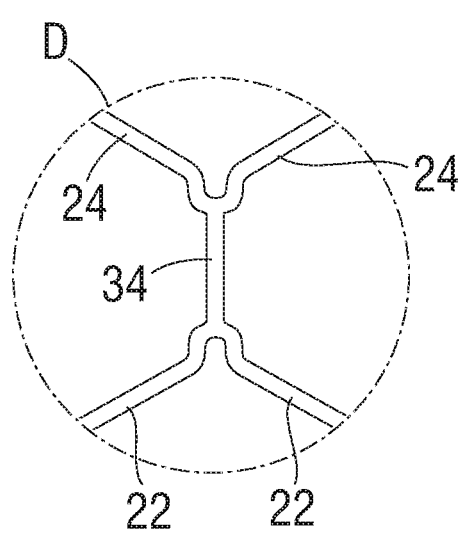
Figure 10:
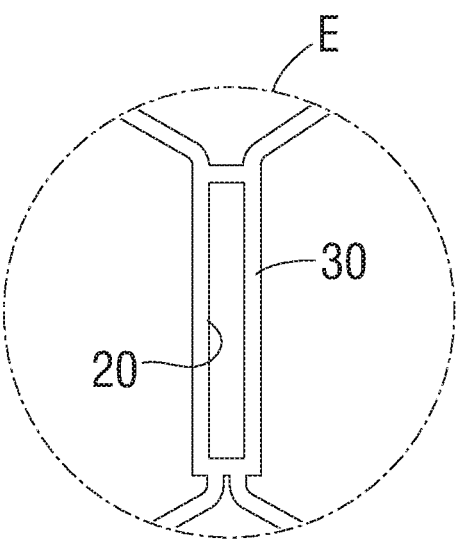

The present disclosure concerns embodiments of implantable prosthetic devices and, in particular, implantable prosthetic valves, and methods for making such devices. In one aspect, a prosthetic device includes encapsulating layers that extend over a fabric layer and secure the fabric layer to another component of the device. In particular embodiments, the prosthetic device comprises a prosthetic heart valve, and can be configured to be implanted in any of the native heart valves. In addition, the prosthetic heart valve can be, for example, a transcatheter heart valve, a surgical heart valve, or a minimally-invasive heart valve. The prosthetic valve also can comprise other types of valves implantable within other body lumens outside of the heart or heart valves that are implantable within the heart at locations other than the native valves, such as trans-atrial or trans-ventricle septum valves.

FIGS. 1-3 show various views of a prosthetic heart valve 10, according to one embodiment. The illustrated valve is adapted to be implanted in the native aortic annulus, although in other embodiments it can be adapted to be implanted in the other native annuluses of the heart. The valve 10 can have four main components: a stent, or frame, 12, a valvular structure 14, and a laminate sealing member 16.

The valvular structure 14 can comprise three leaflets 40, collectively forming a leaflet structure, which can be arranged to collapse in a tricuspid arrangement, as best shown in FIG. 2. The lower edge of leaflet structure 14 desirably has an undulating, curved scalloped shape (suture line 108 shown in FIG. 19F tracks the scalloped shape of the leaflet structure). By forming the leaflets with this scalloped geometry, stresses on the leaflets are reduced which, in turn, improves durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the valve. The leaflets 40 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The bare frame 12 is shown in FIG. 4. The frame 12 can be formed with a plurality of circumferentially spaced slots, or commissure windows, 20 (three in the illustrated embodiment) that are adapted to mount the commissures of the valvular structure 14 to the frame, as described in greater detail below. The frame 12 can be made of any of various suitable plastically-expandable materials (e.g., stainless steel, etc.) or self-expanding materials (e.g., Nitinol) as known in the art. When constructed of a plastically-expandable material, the frame 12 (and thus the valve 10) can be crimped to a radially compressed state on a delivery catheter and then expanded inside a patient by an inflatable balloon or equivalent expansion mechanism. When constructed of a self-expandable material, the frame 12 (and thus the valve 10) can be crimped to a radially compressed state and restrained in the compressed state by insertion into a sheath or equivalent mechanism of a delivery catheter. Once inside the body, the valve can be advanced from the delivery sheath, which allows the valve to expand to its functional size.

Suitable plastically-expandable materials that can be used to form the frame 12 include, without limitation, stainless steel, a nickel based alloy (e.g., a cobalt-chromium or a nickelcobalt-chromium alloy), polymers, or combinations thereof. In particular embodiments, frame 12 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 12 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

Referring to FIGS. 4 and 5, the frame 12 in the illustrated embodiment comprises a first, lower row I of angled struts 22 arranged end-to-end and extending circumferentially at the inflow end 13 of the frame; a second row II of circumferentially extending, angled struts 24; a third row III of circumferentially extending, angled struts 26; a fourth row IV of circumferentially extending, angled struts 28; and a fifth row V of circumferentially extending, angled struts 32 at the outflow end 15 of the frame. A plurality of substantially straight axially extending struts 34 can be used to interconnect the struts 22 of the first row I with the struts 24 of the second row II. The fifth row V of angled struts 32 are connected to the fourth row IV of angled struts 28 by a plurality of axially extending window frame portions 30 (which define the commissure windows 20) and a plurality of axially extending struts 31. Each axial strut 31 and each frame portion 30 extends from a location defined by the convergence of the lower ends of two angled struts 32 to another location defined by the convergence of the upper ends of two angled struts 28. FIGS. 6, 7, 8, 9 and 10 are enlarged views of the portions of the frame 12 identified by letters A, B, C, D and E, respectively, in FIG. 4.

Each commissure window frame portion 30 mounts a respective commissure of the leaflet structure 14. As can be seen each frame portion 30 is secured at its upper and lower ends to the adjacent rows of struts to provide a robust configuration that enhances fatigue resistance under cyclic loading of the valve compared to known cantilevered struts for supporting the commissures of the leaflet structure. This configuration enables a reduction in the frame wall thickness to achieve a smaller crimped diameter of the valve. In particular embodiments, the thickness T of the frame 12 (FIG. 4) measured between the inner diameter and outer diameter is about 0.48 mm or less.

The struts and frame portions of the frame collectively define a plurality of open cells of the frame. At the inflow end of the frame 12, struts 22, struts 24, and struts 34 define a lower row of cells defining openings 36. The second, third, and fourth rows of struts 24, 26, and 28 define two intermediate rows of cells defining openings 38. The fourth and fifth rows of struts 28 and 32, along with frame portions 30 and struts 31, define an upper row of cells defining openings 40. The openings 40 are relatively large and are sized to allow portions of the leaflet structure 14 to protrude, or bulge, into and/or through the openings 40 when the frame 12 is crimped in order to minimize the crimping profile.

As best shown in FIG. 7, the lower end of the strut 31 is connected to two struts 28 at a node or junction 44, and the upper end of the strut 31 is connected to two struts 32 at a node or junction 46. The strut 31 can have a thickness S1 that is less than the thicknesses S2 of the junctions 44, 46. The junctions 44, 46, along with junctions 64, can prevent full closure of openings 40. The geometry of the struts 31, and junctions 44, 46 and 64 can assist in creating enough space in openings 40 in the crimped state to allow portions of the leaflets to protrude (i.e., bulge) outwardly through openings. This allows the valve to be crimped to a relatively smaller diameter than if all of the leaflet material is constrained within the crimped frame.

The frame 12 is configured to prevent or at least minimize possible over-expansion of the valve at a predetermined balloon pressure, especially at the outflow end portion of the frame, which supports the leaflet structure 14. In one aspect, the frame is configured to have relatively larger angles $42a$, $42b$, $42c$, $42d$, $42e$ between struts. The larger the angle, the greater the force required to open (expand) the frame. This phenomenon is schematically illustrated in FIGS. 15A and 15B. FIG. 15A shows a strut 32 when the frame 12 is in its compressed state (e.g., mounted on a balloon). The vertical distance $d_1$ between the ends of the struts is greatest when the frame is compressed, providing a relatively large moment between forces $F_1$ and $F_2$ acting on the ends of the strut in opposite directions upon application of an opening force from inflation of the balloon (or expansion of another expansion device). When the frame expands radially, the vertical distance between the ends of the strut decreases to a distance $d_2$, as depicted in FIG. 15B. As the vertical distance decreases, so does the moment between forces $F_1$ and $F_2$. Hence, it can be seen that a relatively greater expansion force is required as the vertical distance and the moment between the ends of the strut decreases. Moreover, strain hardening (stiffening) at the ends of the strut increases as the frame expands, which increases the expansion force required to induce further plastic deformation at the ends of the strut. As such, the angles between the struts of the frame can be selected to limit radial expansion of the frame at a given opening pressure (e.g., inflation pressure of the balloon). In particular embodiments, these angles are at least 110 degrees or greater when the frame is expanded to its functional size, and even more particularly these angles are at least 120 degrees or greater when the frame is expanded to its functional size.

In addition, the inflow and outflow ends of a frame generally tend to over-expand more so than the middle portion of the frame due to the "dog boning" effect of the balloon used to expand the valve. To protect against over-expansion of the leaflet structure 14, the leaflet structure desirably is secured to the frame 12 below the upper row of struts 32, as best shown in FIG. 1. Thus, in the event that the outflow end of the frame is over-expanded, the leaflet structure is positioned at a level below where over-expansion is likely to occur, thereby protecting the leaflet structure from over-expansion.

In a known valve construction, the leaflets can protrude outwardly beyond the outflow end of the frame when the valve is crimped if the leaflets are mounted too close to the distal end of the frame. If the delivery catheter on which the crimped valve is mounted includes a pushing mechanism or stop member that pushes against or abuts the outflow end of the valve (for example, to maintain the position of the crimped valve on the delivery catheter), the pushing member or stop member can damage the exposed leaflets that extend beyond the outflow end 15 of the frame 12. Another benefit of mounting the leaflets at a location spaced from the outflow end 15 of the frame 12 is that when the valve is crimped on a delivery catheter, the leaflets 40 do not protrude beyond the outflow end 15 of the frame 12 in the axial direction. As such, if the delivery catheter includes a pushing mechanism or stop member that pushes against or abuts the outflow end of the valve, the pushing mechanism or stop member can contact the end of the frame 12, and not leaflets 40, so as to avoid damage to the leaflets.

Also, as can be seen in FIG. 5, the openings 36 of the lowermost row of openings in the frame 12 are relatively larger than the openings 38 of the two intermediate rows of openings. This allows the frame, when crimped, to assume an overall tapered shape that tapers from a maximum diameter $D_1$ at the outflow end of the valve to a minimum diameter $D_2$ at the inflow end of the valve, as shown in FIG. 16 and further described in U.S. Patent Publication No. 2012/0123529, which is incorporated herein by reference. When crimped, the frame 12 has a reduced diameter region extending along a portion of the frame adjacent the inflow end of the frame, indicated by reference number 174, which generally corresponds to the region of the frame covered by the cuff 21 of the laminated sealing member 16, further described below. The diameter of region 174 is reduced compared to the diameter of the upper portion of the frame such that the cuff 21 need not increase the overall crimp profile of the valve. When the valve is deployed, the frame can expand to the cylindrical shape shown in FIG. 4. In one example, the frame of a 26-mm valve, when crimped, had a diameter $D_1$ of 14 French at the outflow end of the valve and a diameter $D_2$ of 12 French at the inflow end of the valve.

Figure 11:
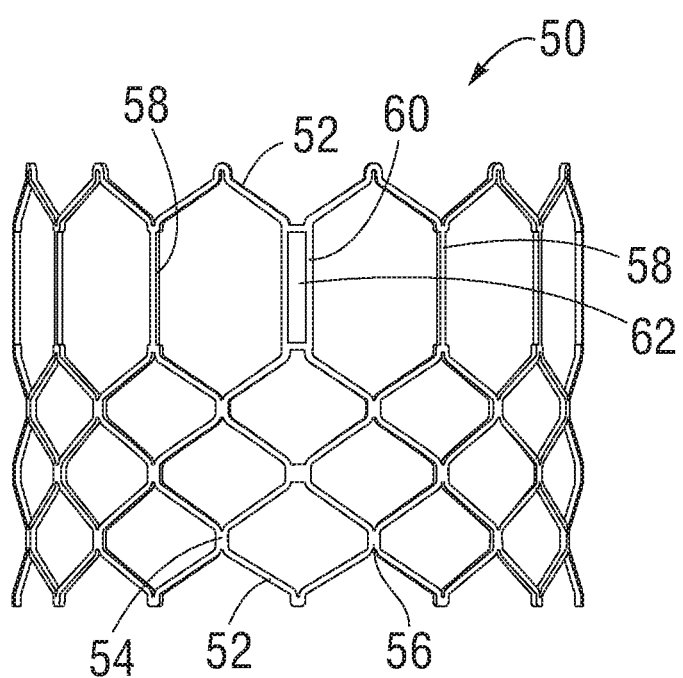

FIGS. 11 and 12 show an alternative frame 50 that can be incorporated in the valve 10. The frame 50 comprises multiple rows of circumferentially extending, angled struts 52 that are connected to each other at nodes, or connecting portions, 54 and 56. The uppermost row of struts 52 are connected to an adjacent row of struts by a plurality of axially extending struts 58 and commissure window frame portions 60. Each commissure frame portion 60 defines a slot or commissure window 62 for mounting a respective commissure of the valvular structure, as described in U.S. Patent Publication No. 2012/0123529 incorporated by reference above. In particular embodiments, the thickness T of the frame 50 is about 0.45 mm or less. FIGS. 13 and 14 are enlarged views of the portions of the frame 50 identified by letters A and B, respectively, in FIG. 12.

The laminate sealing member 16 can include a main portion 17 extending from the proximal end of the fourth row IV of angled struts 28 (i.e., from about the height of the commissure windows 20), and an end portion 19 extending from the inflow end 13 of the frame 12, as shown in FIGS. 1-3. In the illustrated embodiment, the end portion 19 can be folded back on itself and secured to the main portion 17 to form a cuff 21 adjacent the inflow end 13 of the frame 12, as shown in FIGS. 1-3, and 18. The end portion 19 can include a plurality of circumferentially spaced apart extension portions or projections 23 that can be secured to the main portion 17 by, for example, heat bonding, adhesive, and/or suturing, as further described below. The laminate sealing member 16 can seal against the tissue of the native valve annulus, helping to reduce paravalvular leakage past the prosthetic valve 10. In some embodiments, the cuff 21 can billow open such that it defines a pocket in the laminate sealing member 16 extending circumferentially around the inflow end 13 of the frame 12 when the prosthetic valve is implanted in a native valve annulus. Alternatively, the end portion 19 can lie relatively flush against the main portion 17, as desired.

The laminate sealing member 16 can comprise inner and outer encapsulating layers 84, 86, respectively (also referred to as "inner and outer layers"), as shown in FIGS. 17 and 18. In particular embodiments, the encapsulating layers 84, 86 comprise a non-fabric polymer layer or film. In some embodiments, the laminate sealing member 16 can also include a reinforcing layer, such as a fabric or textile layer 18 situated adjacent the frame 12 between the encapsulating layers 84, 86. The encapsulating layers 84, 86 can be fused, bonded, or otherwise secured to each other through the openings in the frame 12, which effectively encapsulates corresponding portions of the frame 12 and the fabric layer 18 to secure these components in their assembled state shown in FIGS. 1-3.

In the embodiment shown, the inner and outer encapsulating layers 84, 86 can be coextensive along the axial length of the main portion 17 of the laminate sealing member 16. In other words, the encapsulating layers 84, 86 can both extend distally from about the level of the commissure windows 20 to the inflow end of the frame to completely or substantially encapsulate the corresponding portion of the frame 12 and the fabric layer 18, as shown in FIG. 18. In the illustrated embodiment, the inner layer 84 can terminate at or near the inflow end 13 of the frame 12, while the outer layer 86 can extend beyond the inflow end to form the end portion 19 of the laminate sealing member 16 and, hence, the cuff 21. Thus, in the illustrated embodiment, the inner layer 84 forms an inner skirt of the sealing member and the outer layer 86 forms an outer skirt of the sealing member. In alternative embodiments, the inner and/or outer layers 84, 86 can extend along any proportion of the main portion 17 or the end portion 19 of the laminate sealing member 16, as desired. For example, in some embodiments the inner and outer layers 84, 86 can be coextensive along both the main portion 17 and the end portion 19 of the laminate sealing member 16. In further alternative embodiments, the outer layer 86 can terminate at the inflow end 13 of the frame 12, while the inner layer 84 can continue beyond the inflow end 13 to form the cuff 21. In the illustrated embodiment, the outer layer 86 can form a fold line at an upstream-most end of the outer layer. The outer layer 86 can double back on the outside of the frame so that the cuff 21 extends from the fold line in a downstream direction along an outer surface of a main body portion of the outer layer and forms a double layer on the exterior of the frame 12.

In some embodiments, the layers 84, 86 can be such that they only encapsulate selected portions of the frame 12 and the fabric layer 18. Also, although in the illustrated embodiment the inner and outer layers 84, 86 are tubular or cylindrical in shape, the inner and outer layers 84, 86 need not extend along the respective inner and outer surfaces of the frame 12 in the circumferential direction through 360 degrees. In other words, the inner and outer layers 84, 86 can have a cross-sectional profile (in a plane perpendicular to the axis of the lumen of the valve) that is not a complete circle.

As stated above, the laminate sealing member 16 can comprise a reinforcing layer, such as the fabric layer 18. The fabric layer 18 can comprise, for example, any of various woven fabrics, such as gauze, polyethylene terephthalate (PET) fabric (e.g., Dacron), polyester fabric, polyamide fabric, or any of various non-woven fabrics, such as felt. The thickness of the fabric layer can vary, but can be less than 6 mil, and desirably less than 4 mil, and even more desirably about 2 mil. Traditionally, fabric skirts have been secured to frames using sutures. In contrast, in the illustrated embodiment, fabric layer 18 desirably is secured to the frame 12 without sutures and instead is secured to the frame 12 with the inner and/or outer encapsulating layers 84, and 86 (see, e.g., FIGS. 17 and 18).

The fabric layer 18 of the prosthetic valve can serve several functions. In particular embodiments, for example, the fabric layer 18 primarily functions to strengthen the laminate sealing member 16 to resist tearing. In this manner, the leaflet structure 14 can be anchored to the frame 12 by sutures without tearing the laminate sealing member 16. In addition, the fabric layer 18, in cooperation with the encapsulating layers 84, 86, can help decrease (or prevent) paravalvular leakage past the prosthetic valve when in the expanded configuration.

Alternatively, the reinforcing layer can comprise one or more layers or films formed from any of various semi-crystalline polymeric materials or thermoplastics having aligned or partially aligned (e.g., parallel) molecular chains. Such materials can exhibit anisotropic mechanical properties, such as increased mechanical strength along the longitudinal direction of the molecular chains. Suitable semi-crystalline polymeric materials can include, for example, PTFE, PET, polypropylene, polyamide, polyetheretherketone (PEEK), etc., layers or films of which can be situated between and encapsulated by the encapsulating layers to reinforce the laminate sealing member 16.

The encapsulating layers 84, 86 can be made of any suitable biocompatible material. In one example, the encapsulating layers 84, 86 can be formed using an electrospinning process. In other examples, the encapsulating layers 84, 86 can be formed using any other suitable method including, for example, dip coating, spray coating, or melt-spinning. The biocompatible material may be a non-absorbable polymeric material (i.e., a material that does not dissolve once implanted in the body). Examples of such materials include, without limitation, expanded polytetrafluoroethylene (ePTFE), unexpanded porous PTFE, polyester or expanded PTFE yarns, PTFE, ultrahigh molecular weight polyethylene (UHMWPE), other polyolefins, composite materials such as ePTFE with PTFE fibers, or UHMWPE film with embedded UHMWPE fibers, polyimides, silicones, polyurethane, hydrogels, fluoroethylpolypropylene (FEP), polypropylfluorinated amines (PFA), other related fluorinated polymers, or various combinations of any of these materials. In particular embodiments, the encapsulating layers 84, 86 are formed from respective tubes made of a suitable polymeric material (e.g., ePTFE tubes or UHMWPE tubes) that are bonded to each other when subjected to heat treatment, as described in detail below.

Microporous expanded polytetrafluoroethylene (ePTFE) tubes can be made by a number of well-known methods. Expanded PTFE is frequently produced by admixing particulate dry polytetrafluoroethylene resin with a liquid lubricant to form a viscous slurry. The mixture can be poured into a mold, typically a cylindrical mold, and compressed to form a cylindrical billet. The billet can then be ram extruded through an extrusion die into either tubular or sheet structures, termed extrudates in the art. The extrudates comprise an extruded PTFE-lubricant mixture called "wet PTFE." Wet PTFE has a microstructure of coalesced, coherent PTFE resin particles in a highly crystalline state. Following extrusion, the wet PTFE can be heated to a temperature below the flash point of the lubricant to volatilize a major fraction of the lubricant from the PTFE extrudate. The resulting PTFE extrudate without a major fraction of lubricant is known in the art as dried PTFE. The dried PTFE can then be either uniaxially, biaxially, or radially expanded using appropriate mechanical apparatus known in the art. Expansion is typically carried out at an elevated temperature, e.g., above room temperature but below 327 degrees C., the crystalline melt point of PTFE. Uniaxial, biaxial, or radial expansion of the dried PTFE causes the coalesced, coherent PTFE resin to form fibrils emanating from nodes (regions of coalesced PTFE), with the fibrils oriented parallel to the axis of expansion. Once expanded, the dried PTFE is referred to as expanded PTFE ("ePTFE") or microporous PTFE.

UHMWPE is made up of very long chains of polyethylene, with molecular weight numbering in the millions, usually between 2 and 6 million. It is highly resistant to corrosive chemicals, has extremely low moisture absorption and a very low coefficient of friction. It is self-lubricating and highly resistant to abrasion. UHMWPE is processed using compression molding, ram extrusion, gel spinning, and sintering. UHMWPE is available commercially as a powder, in sheets or rods, and as fibers.

Referring to FIGS. 19A-19E and 20, an exemplary method for forming the prosthetic valve 10 will now be described. Although the use of ePTFE is described below, it is merely exemplary in nature and is not intended as a limitation. It is to be understood that other materials such as UHMWPE, polyurethane composite materials, or any other non-absorbable polymeric materials described above can be used.

First, as depicted in FIG. 19A, an inner layer 84 comprising a flat piece of ePTFE material or an ePTFE tube can be placed or wrapped on a mandrel 100. Second, as depicted in FIG. 19B, a frame 12 can be placed over the inner layer 84 such that the inner layer 84 extends from approximately the commissure windows 20 to the inflow end 13 of the frame 12, although it will be appreciated that other configurations are possible. Third, as depicted in FIG. 19C, the fabric layer 18 can be placed over the frame 12. The fabric layer 18 can be in the form of a sheet of fabric material that is tightly wrapped around the outer surface of the frame 12. However, in alternative embodiments, the fabric layer 18 may also be situated inside the frame 12 (e.g., placed on the inner layer 84 before placement of the frame 12 on the inner layer 84). In the illustrated embodiment, the fabric layer 18 may have an axial length that is shorter than the inner and outer layers 84, 86 to facilitate bonding of the inner and outer layers 84, 86 at their respective ends to encapsulate the frame 12 and fabric layer 18 therebetween.

Figure 19D:
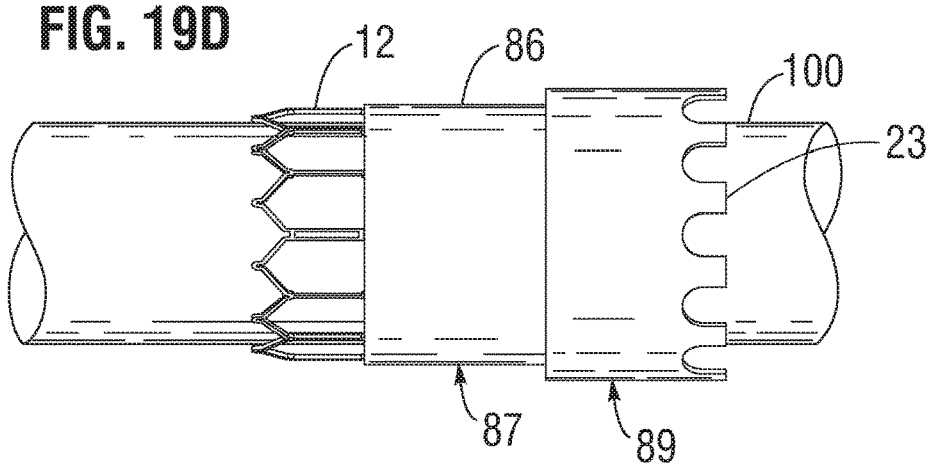
Figure 19E:
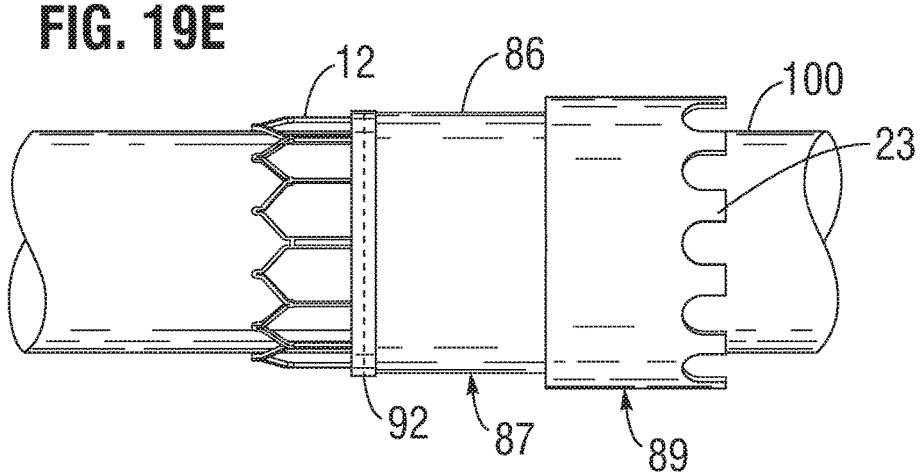

Fourth, as depicted in FIG. 19D, the outer layer 86 comprising a flat piece of ePTFE material or an ePTFE tube can be placed or wrapped over the fabric layer 18. In the illustrated embodiment, the outer layer 86 can have a proximal portion 87 and a distal portion 89, wherein the distal portion 89 can have a diameter that is greater than the diameter of the proximal portion 87. The extension portions 23 of the outer layer 86 can be formed on the distal portion 89 (e.g., by laser cutting) before or after placement of the outer layer 86 on the mandrel 100, as desired. As shown in FIG. 19E, layers of PTFE tape 92 can then be wrapped around one or both ends of the outer layer 86 to help secure the position of the outer layer 86 to the underlying layers of the assembly and to the mandrel 100 during subsequent processing.

An alternative way to encapsulate the frame with a polymer is by using an electrospinning technique. Electrospinning uses an electrical charge to draw very fine (typically on the micrometer or nanometer scale) fibers from a liquid.

The assembly shown in FIG. 19E can now undergo an encapsulation process whereby the assembly is subjected to heat and/or pressure to cause the inner and outer layers 84, 86 to bond to each other through the openings in the frame 12 proximally and distally of the fabric layer 18 (see FIG. 18) to encapsulate the frame 12 and the fabric layer 18 therebetween. Depending on the porosity of the weave of the fabric layer 18, the layers 84, 86 can bond to each other through the fabric layer 18. During this step, the entire outer surface of the assembly on the mandrel 100 can be tightly wrapped with a suitable material (e.g., PTFE tape) to apply pressure to the various layers of the assembly such that the layers 84, 86 form a monolithic laminate sealing member 16. The entire assembly, including the mandrel 100, can be transferred to an oven where the inner and outer layers 84, 86 are sintered by being heated to a predetermined temperature. In one implementation, for example, the inner and outer layers 84, 86 are sintered by being heated to a temperature above 327 degrees C., the crystalline melt point of PTFE. In some embodiments, bonding between the inner and outer layers 84, 86 can be facilitated by the use of one or more adhesives, such as polyurethane.

During the sintering process the ePTFE is restrained against uniaxial, biaxial, or radial contraction. Sintering can cause at least a portion of the crystalline PTFE to change from a crystalline state to an amorphous state. The conversion from a highly crystalline structure to one having an increased amorphous content can lock the node and fibril microstructure, as well as its orientation relative to the axis of expansion, and provide a dimensionally stable tubular or sheet material upon cooling.

After the sintering process, the assembly is removed from the oven and allowed to cool. The material wrapped around the assembly, as well as tape layers 92, can now be removed. Any portions of the inner and outer layers 84, 86 that extend beyond the desired dimensions of the laminate sealing member 16 can be trimmed. If desired, selected portions of the inner and outer layers 84, 86 can be removed to facilitate crimping of the valve for delivery into a patient. Any of various suitable techniques and mechanisms can be used to selectively remove portions of layers 84, 86, such as laser cutting. For example, portions of the inner and outer layers 84, 86 that cover selected openings in the frame 12 can be cut or otherwise removed to minimize the amount of material in the valve, which can facilitate crimping of the valve to a relatively small diameter.

Figure 19F:
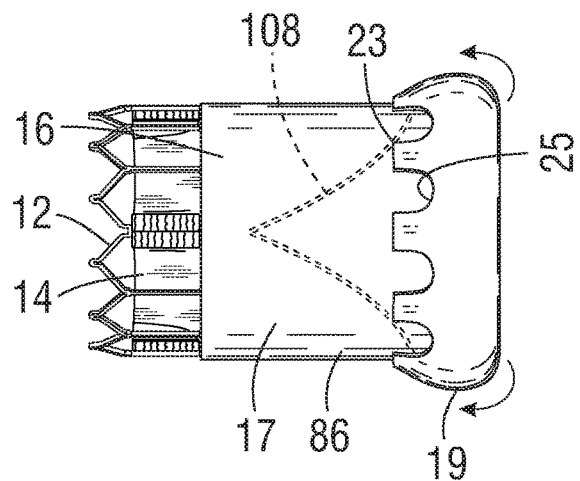

Referring to FIG. 19F, after the encapsulating layers 84, 86 have been bonded together to form the laminate sealing member 16, the end portion 19 of the laminate sealing member 16 can be folded over to form the cuff 21, and the extension portions 23 can be secured to the main portion 17 of the laminate sealing member 16. In some embodiments, the extension portions 23 can be attached to the main portion 17 by heat bonding (e.g., in combination with an optional additional polymer such as polyurethane to promote bonding between the ePTFE layers, with process temperatures adjusted as necessary). In some embodiments, the extension portions 23 can be attached to the main portion by suturing. In some embodiments, the end portion 19 and/or the extension portions 23 can include a reinforcing fabric layer to facilitate suturing of the end portion 19 to the main portion 17. In some embodiments, the cuff 21 can be secured to the main portion via heat bonding, an adhesive, and/or suturing.

In particular embodiments, the cuff 21 is secured to the main body 17 only along the uppermost edges of the extension portions 23 and the U-shaped upper edge portions 25 defining the gaps are not secured to the frame. Thus, the cuff 21 can form a pocket having openings defined by the U-shaped edges 25.

In an alternative embodiment, the fabric layer 18 can be pre-formed in a tubular or cylindrical configuration. In this embodiment, the fabric layer 18 can be positioned on the frame 12 by first partially crimping the frame 12 to a diameter smaller than the diameter of the fabric layer 18. The fabric layer 18 can then be placed over the partially crimped frame, and the frame can be expanded back to its functional size. The fabric layer 18 desirably is sized such that the expanded frame 12 applies at least some outward radial pressure against the fabric layer 18 to assist in retaining the fabric layer 18 on the frame 12. The frame and fabric layer assembly can then be placed onto inner layer 84 (already on the mandrel), and encapsulated following the process described above. In another embodiment, the fabric layer 18 can be placed on the inside of the frame 12. For example, the fabric layer 18 can be in the form of a sheet of material that is wrapped around inner layer 84 prior to placing the frame 12 on the mandrel 100. Alternatively, the fabric layer 18 can have a tubular configuration and can be positioned onto inner layer 84 prior to placing the frame 12 on the mandrel 100.

After encapsulation, the frame 12 can be removed from the mandrel 100 and the leaflet structure 14 can be attached to the fabric layer 18 and/or the frame 12 using sutures or other suitable techniques or mechanisms. In the illustrated embodiment shown in FIG. 2, for example, the leaflets 40 are secured to one another at their adjacent sides to form commissures 48. Each commissure 48 can be secured to a corresponding commissure window 20 of the frame 12, as described in U.S. Patent Publication No. 2012/0123529, incorporated by reference above. The lower, or inflow, end portion of the leaflets 40 can be sutured to the fabric layer 18 of the laminate sealing member 16 along a suture line 108 that tracks the curvature of the scalloped lower edge of the leaflet structure, as shown in FIG. 19F. The fabric layer 18 can provide the strength required to retain the sutures without tearing the laminate sealing member 16. Any suitable suture, such as an Ethibond suture, can be used to secure the leaflets 40 to the fabric layer 18 of the laminate sealing member 16 along suture line 108.

In certain embodiments, the lower edges of the leaflets 40 can be secured to the fabric layer 18 via a thin PET reinforcing strip (not shown), as disclosed in U.S. Pat. No. 7,993,394, which is incorporated herein by reference. As described in U.S. Pat. No. 7,993,394, the reinforcing strip can be sutured to the lower edges of the leaflets. The reinforcing strip and the lower edges of the leaflets can then be sutured to the laminate sealing member 16 along suture line 108. The reinforcing strip desirably is secured to the inner surfaces of the leaflets 40 such that the lower edges of the leaflets become sandwiched between the reinforcing strip and the laminate sealing member 16 when the leaflets and the reinforcing strip are secured to the laminate sealing member. The reinforcing strip enables a secure suturing and protects the pericardial tissue of the leaflet structure from tears.

As noted above, the conventional method for securing a fabric skirt to a frame involves manually suturing the fabric skirt to the frame. In contrast, the illustrated embodiment relies on the inner and outer layers 84, 86 to secure the fabric layer 18 in place relative to the frame. As can be appreciated, this technique for securing the fabric layer 18 to the frame can significantly reduce the amount of labor required to assemble a valve. The use of layers 84, 86 provides other advantages as well. For example, the outer layer 86, when formed from ePTFE or UHMWPE, has a porous microstructure that facilitates tissue in-growth from surrounding tissue after the valve is implanted. When formed of ePTFE, UHMWPE, or other suitable polymers, the laminate sealing member 16 can exhibit lower blood permeability than conventional fabric skirts, especially in the period immediately following implantation, which can help to reduce paravalvular leakage.

In addition, the inner and outer layers 84, 86 can protect the leaflets 40 during crimping and facilitate even and predictable crimping of the valve. When a prosthetic valve is placed in a crimping apparatus to radially compress the valve to a smaller diameter for insertion into a patient, the leaflets of the valve are pressed against the inner surface of the metal frame and portions of the tissue can protrude into the open cells of the frame between the struts and can be pinched due to the scissor-like motion of the struts of the frame. If the valve is severely crimped to achieve a small crimping size, this scissor-like motion can result in cuts and rupture of the tissue leaflets. To protect the leaflets during crimping, it is known to place a deformable material around the valve to prevent direct contact between the hard surface of the jaws of the crimping apparatus and the valve. The deformable material can protrude into the open cells, thereby preventing the leaflets from entering this space and being pinched by metal struts of the frame. Layers 84, 86 function in a manner similar to this deformable material to protect leaflets from being pinched during crimping. As such, the disclosed valve 10 can be placed in a crimping apparatus without an additional protective layer of material surrounding the valve. Due to the presence of layers 84, 86, the valve 10 can be crimped onto the balloon of a balloon catheter in an even and predictable manner that forms a very ordered structure of balloon-leaflets-frame (from inward to outward). Additionally, inner layer 84 can prevent direct contact between the leaflets 40 and the frame 12 during working cycles of the valve (i.e., as the valve leaflets open and close in response to blood pressure) to protect the leaflets against damage caused by contact with the frame.

Moreover, as noted above, the fabric layer 18 can be any of various woven or non-woven fabrics, such as a gauze, PET cloth, or felt. PET or other fabrics are substantially non-elastic (i.e., substantially non-stretchable and non-compressible). As such, in known prosthetic valves, the skirt can wrinkle after expansion from the crimped diameter. In the illustrated embodiment, the fabric layer 18 can be tightly compressed against the frame by layers 84, 86 such that when the valve is expanded to its functional size from the crimped state, the fabric layer 18 can recover to its original, smooth surfaces with little or no wrinkling.

The encapsulation process is described above in the context of securing a fabric layer to the frame of an expandable transcatheter heart valve within a laminate sealing member. The fabric layer typically is more durable than the ePTFE layers and, therefore, the fabric layer reinforces the ePTFE layers where they undergo stresses from cyclic loading of the valve. However, in alternative embodiments, the valve can be formed without the fabric layer to permit crimping of the valve to a smaller delivery diameter. The ePTFE layers 84, 86, and the cuff 21 can serve as the primary sealing mechanism that prevents paravalvular leakage around or through the frame of the valve. In other embodiments, the fabric layer 18 can be used to reinforce only selected portions of the layers 84, 86, such as those portions of layers 84, 86 subject to greatest loading, while the remaining portions of layers 84, 86 do not contain a fabric layer or fabric layer.

It should be noted that the encapsulation process can be utilized to secure a fabric or woven or non-woven textile element to other components of a prosthetic valve. For example, surgical valves (valves which are typically implanted via open-heart surgery) include several components that are covered with a cloth or fabric material. Known surgical valves typically have a sewing ring and one or more stent components, each of which are covered with a cloth member. The cloth member typically is wrapped around the valve component and the longitudinal edges of the cloth member are manually stitched to each other to secure the cloth member around the valve component. As can be appreciated, the time and labor required to secure such cloth members to the components of the valve can be significantly reduced by employing an encapsulation technique as described herein.

Figure 20:
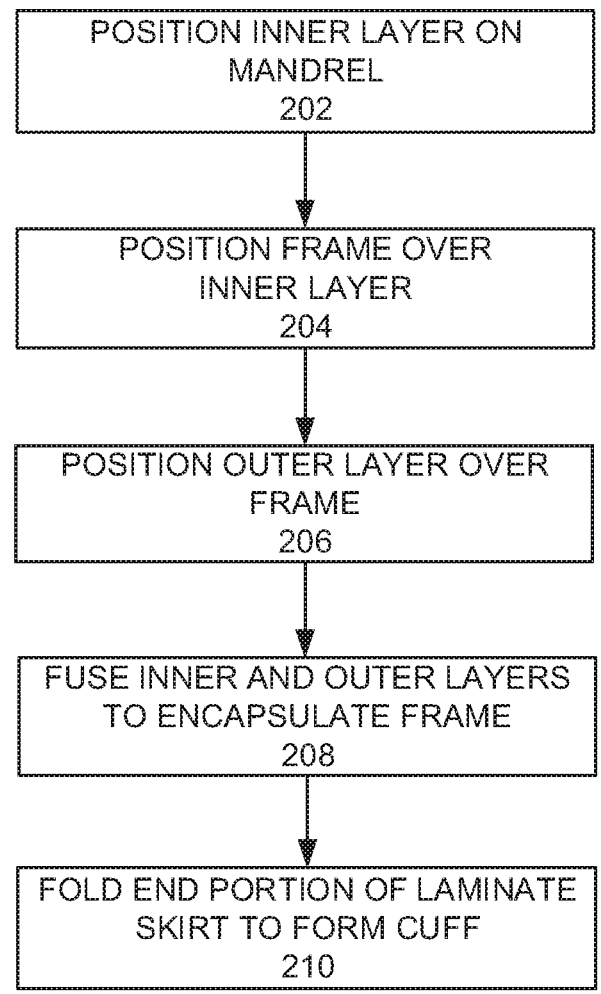
FIG. 20 is a flow chart of a method for forming a laminate sealing member on the frame of a prosthetic heart valve, according to one embodiment.

FIG. 20 schematically illustrates a representative method of encapsulating a frame of a prosthetic valve to form a laminate sealing member. At block 202, an inner layer comprising, for example, ePTFE, can be positioned over a mandrel.

At block 204, a frame can be positioned on the mandrel over the inner layer.

At block 206, an outer layer comprising, for example, ePTFE, can be positioned on the mandrel over the frame.

At block 208, the inner and outer layers can be fused to one another to create a laminate sealing member encapsulating at least a portion of the frame therebetween.

At block 210, an end portion of the laminate sealing member can be folded up and secured to a main portion of the laminate sealing member to form a cuff. The laminate sealing member can optionally include a fabric or textile layer located between the inner and outer layers adjacent the inside or outside of the frame, as described above.

FIGS. 21-24 illustrate another embodiment of a sealing member 300 including a main portion 302, an intermediate portion 304, and an end portion 306. In the illustrated embodiment, the main portion 302 can have a diameter $D_M$ corresponding substantially to an inner diameter of an expanded frame 308. In the illustrated embodiment, the end portion 306 can have a diameter $D_E$ that is equal to or greater than an outer diameter of the expanded frame 308, and the intermediate portion 304 can have a diameter that increases or flares in a longitudinal direction of the sealing member from the diameter $D_M$ of the main portion 302 to the diameter $D_E$ of the end portion 306. Thus, in the illustrated embodiment, the intermediate portion can have a frusto-conical shape.

The end portion 306 of the sealing member 300 can be folded (e.g., along the interface 316 between the intermediate portion and the end portion and the interface 318 between the main portion and the intermediate portion) and secured to the main portion 302, as shown in FIGS. 21 and 22. During the assembly process, the sealing member can be secured to the inside of the frame 308 such that the main portion 302 is adjacent an inner surface of the frame and the end portion 306 extends distally from an inflow end 310 of the frame 308. The end portion 306 can then be folded upwardly and around the inflow end 310 of the frame and attached to the main portion 302 (through the frame) and/or to the exterior of the frame 308 to form a cuff 312 adjacent the inflow end 310 of the frame. In this manner, the sealing member 300 can combine the functions of conventionally separate inner and outer skirts into a single unitary sealing member. This can reduce the amount of material around the inflow end of the valve, thereby reducing the crimped profile of the valve, along with flow disturbances or obstructions created by the sealing member when inserted into a native heart valve. Use of the sealing member described herein can also reduce the time and labor required to assemble a valve over known valve skirts.

In the illustrated embodiment, the end portion 306 can include tabs or projections 314, which can be secured to the main portion 302 of the sealing member and/or to the exterior of the frame members by, for example, stitching, adhesive, heat bonding, etc. The projections 314 can aid in folding the end portion 306 to form the cuff 312, thereby reducing the need for complex shaping of the sealing member. In some embodiments, the main portion 302 can also include tabs or projections.

The sealing member 300 may be made from any of various woven fabrics such as PET, polybutylene terephthalate (PBT), UHMWPE, polypropylene, natural fibers such as silk, etc. The fabric may be woven or braided into the final shape of the sealing member 300. Alternatively, the sealing member 300 may be formed from a tubular piece of material, such as by application of heat or by shape setting. The projections 314 can be created by, for example, cutting sections of material from the end portion 306. Additionally, it should be understood that the shape of the sealing member 300 can be applicable to any of the sealing members described herein.

In some embodiments, the properties of the fabric may be varied along the length of the sealing member. For example, yarns in the fabric of the main portion 302 may be set at an angle (e.g., 45 degrees) such that the fabric of the main portion can more easily elongate and/or foreshorten during crimping and expansion of the frame.

In some embodiments, a fabric sealing member (e.g., the sealing member 300) can be laminated with or encapsulated between one or more layers or films of ePTFE (e.g., 0.00020 inch to 0.001 inch Aeos® ePTFE material available from Zeus Industrial Products, Inc.). For example, one or more layers of ePTFE can be applied to at least one surface of the sealing member to reduce the permeability of the sealing member. This can reduce the amount of blood leakage through the sealing member, especially in the time period immediately following implantation. The smooth surface of the one or more ePTFE layers can also improve the durability of the tissue leaflets contacting the ePTFE layers, and can reduce or prevent the exposure of broken yarns or filaments in the underlying fabric, improving yields during manufacturing of the heart valves. The number and thickness of the one or more ePTFE layers, along with other parameters including the internodal distance, porosity, etc., of the ePTFE, can be varied according to the particular properties desired. In alternative embodiments, one or more layers of ePTFE are applied to both surfaces of a sealing member (e.g., sealing member 300) before it is assembled onto a frame.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims.

What is claims is:

1. An implantable prosthetic valve that is radially collapsible to a collapsed configuration and radially expandable to an expanded configuration, the prosthetic valve comprising:
    an annular frame having an inflow end and an outflow end;
    a leaflet structure positioned within the frame and secured thereto; and
    a laminate sealing member comprising an inner layer positioned on the inside of the frame and an outer layer positioned on the outside of the frame, the outer layer including an inflow end portion comprising an inflow edge, an outflow end portion comprising an outflow edge, and a main body portion extending between the inflow end portion and the outflow end portion, the inflow end portion of the outer layer extending from the inflow end of the frame, the inner and outer layers being heat-bonded together to form a main portion of the laminate sealing member that encapsulates corresponding portions of the frame;
    wherein the inflow end portion of the outer layer is folded to form a cuff adjacent the inflow end of the frame such that the outer layer forms a fold line at an upstream-most end of the outer layer and doubles back on the outside of the frame so that the cuff extends from the fold line in a downstream direction along an outer surface of the main body portion of the outer layer and forms a double layer on the exterior of the frame, and wherein the inflow edge of the outer layer is secured to the main body portion of the outer layer downstream of the fold line.

2. The prosthetic valve of claim 1, further comprising a reinforcing layer positioned adjacent the frame and encapsulated between the inner and outer layers.

3. The prosthetic valve of claim 2, wherein the leaflet structure is sutured to the reinforcing layer.

4. The prosthetic valve of claim 2, wherein the reinforcing layer comprises a fabric.

5. The prosthetic valve of claim 2, wherein the reinforcing layer comprises a semi-crystalline polymeric material.

6. The prosthetic valve of claim 1, wherein the inflow end portion of the outer layer comprises extension portions secured to the main body portion of the outer layer.

7. The prosthetic valve of claim 1, wherein the inflow edge of the outer layer is secured to the main body portion of the outer layer by heat bonding.

8. The prosthetic valve of claim 1, wherein the inflow edge of the outer layer is secured to the main body portion of the outer layer by suturing.

9. The prosthetic valve of claim 1, wherein the laminate sealing member comprises a non-absorbable polymer selected from expanded polytetrafluoroethylene, unexpanded porous polytetrafluoroethylene, ultrahigh molecular weight polyethylene, or any combination thereof.

10. The prosthetic heart valve of claim 1, wherein the entire inflow end portion of the outer layer is radially outward of an inflow end portion of the inner layer.

11. The prosthetic heart valve of claim 1, wherein the fold line of the outer layer is radially outward of an outer surface of the main body portion of the outer layer.

12. A method of making a prosthetic heart valve, comprising:
    positioning an inner layer about a mandrel;
    positioning an annular radially expandable and collapsible frame over the inner layer such that the inner layer is positioned on the inside of the frame, the frame having an inflow end and an outflow end;
    positioning an outer layer over the frame, the outer layer including an inflow end portion comprising an inflow edge, an outflow end portion comprising an outflow edge, and a main body portion extending between the inflow end portion and the outflow end portion, the outer layer being positioned such that the outer layer is on the outside of the frame, and such that the inflow end portion of the outer layer extends beyond the inflow end of the frame;
    heat-bonding the inner and outer layers to form a monolithic laminate sealing member such that at least a portion of the frame is encapsulated within a main portion of the laminate sealing member;
    folding the inflow end portion of the outer layer to form a cuff adjacent the inflow end of the frame such that the outer layer forms a fold line at an upstream-most end of the outer layer and doubles back on the outside of the frame so that the cuff extends from the fold line in a downstream direction along an outer surface of the main body portion of the outer layer and forms a double layer on the exterior of the frame;
    securing the inflow edge of the outer layer to the main body portion of the outer layer downstream of the fold line;
    positioning a leaflet structure within the frame; and
    securing the leaflet structure to the frame.

13. The method of claim 12, wherein the heat-bonding further comprises:
    applying pressure to force the outer layer and the inner layer into contact with one another; and
    heating the inner and outer layers so that they heat-bond together to form the laminate sealing member encapsulating the frame.

14. The method of claim 12, further comprising positioning a reinforcing layer adjacent the frame between the inner and outer layers.

15. The method of claim 14, wherein the reinforcing layer comprises at least one of a fabric material, a textile material, or a semi-crystalline polymeric material.

16. The method of claim 12, wherein securing the inflow edge of the outer layer to the main body portion of the outer layer further comprises heat bonding the inflow edge of the outer layer to the main body portion of the outer layer.

17. The method of claim 12, wherein securing the inflow edge of the outer layer to the main body portion of the outer layer further comprises suturing the inflow edge of the outer layer to the main body portion of the outer layer.

18. The method of claim 12, wherein securing the inflow edge of the outer layer to the main body portion of the outer layer further comprises securing extension portions of the inflow end portion of the outer layer to the main body portion of the outer layer.

19. A transcatheter heart valve, comprising:
a radially expandable frame having an inflow end, an outflow end, and a laminate sealing member comprising:
   a non-fabric inner layer positioned inside of the frame;
   a non-fabric outer layer positioned outside of the frame, the non-fabric outer layer comprising an inflow end portion including an inflow edge, an outflow end portion comprising an outflow edge, and a main body portion extending between the inflow end portion and the outflow end portion, the inflow end portion of the non-fabric outer layer extending beyond the inflow end of the frame; and
   a fabric layer positioned between the non-fabric inner layer and the non-fabric outer layer, the non-fabric inner and outer layers being heat-bonded to one another such that the fabric layer and at least a portion of the frame are encapsulated therebetween;
wherein the inflow end portion of the non-fabric outer layer is folded to form a cuff adjacent the inflow end of the frame such that the non-fabric outer layer forms a fold line at an upstream-most end of the outer layer and doubles back on the outside of the frame so that the cuff extends from the fold line in a downstream direction along an outer surface of the main body portion of the non-fabric outer layer and forms a double layer on the exterior of the frame, and wherein the inflow edge of the non-fabric outer layer is secured to the main body portion of the non-fabric outer layer downstream of the fold line.

20. The transcatheter heart valve of claim 19, wherein the fold line of the outer layer is radially outward of an outer surface of the main body portion of the outer layer.

* * * * *